United States Patent [19]

Levy

[11] Patent Number: 5,691,060

[45] Date of Patent: Nov. 25, 1997

[54] UTILIZATION OF A TRANSACYLATION REACTION BETWEEN AN ESTERIFIED POLYSACCHARIDE AND A POLYAMINATED OR POLYHYDROXYLATED SUBSTANCE FOR FABRICATING MICROPARTICLES, MICROPARTICLES THUS OBTAINED, METHODS AND COMPOSITIONS CONTAINING THEM

[75] Inventor: Marie-Christine Levy, Reims, France

[73] Assignee: Coletica, Lyons, France

[21] Appl. No.: 387,776

[22] PCT Filed: Aug. 4, 1993

[86] PCT No.: PCT/FR93/00792

§ 371 Date: Feb. 21, 1995

§ 102(e) Date: Feb. 21, 1995

[87] PCT Pub. No.: WO94/04261

PCT Pub. Date: Mar. 3, 1994

[30] Foreign Application Priority Data

Aug. 20, 1992 [FR] France ..................... 92 10173

[51] Int. Cl.$^6$ ..................................................... B32B 9/00
[52] U.S. Cl. ................... 428/402.21; 528/272; 424/408; 424/451; 424/455; 424/457; 424/468; 424/491; 424/493; 424/497; 424/499; 264/4.32; 264/4.33; 264/4.4; 428/402.21
[58] Field of Search ............... 528/272; 424/408, 424/451, 455, 457, 468, 491, 493, 497, 499; 264/4.32, 4.33, 4.4; 428/402.21

[56] References Cited

U.S. PATENT DOCUMENTS

| | | | |
|---|---|---|---|
| 3,833,744 | 9/1974 | Bomstein | 426/652 |
| 4,187,194 | 2/1980 | Wellman et al. | 252/316 |
| 4,217,370 | 8/1980 | Rawlings et al. | 426/98 |
| 4,497,793 | 2/1985 | Simkin | 424/32 |
| 4,814,176 | 3/1989 | Makino et al. | 424/457 |
| 5,051,304 | 9/1991 | David et al. | 428/402.2 |
| 5,227,274 | 7/1993 | Ishikawa et al. | 430/138 |
| 5,362,424 | 11/1994 | Lee et al. | 264/4.3 |

FOREIGN PATENT DOCUMENTS 0 273 823  7/1988  European Pat. Off. .

*Primary Examiner*—Samuel A. Acquah
*Attorney, Agent, or Firm*—Larson & Taylor

[57] ABSTRACT

The invention relates to microparticles, particularly microcapsules and their fabrication method. Said microparticles, and particularly said microcapsules, are characterized in that they have a wall made of the product obtained from the reaction between a polysaccharide carrying esterified carboxylic groups and a polyaminated or polyhydroxylated substance, particularly through a transacylation reaction. Said microparticles or said microcapsules are useful for the fabrication of cosmetic, pharmaceutical or food product compositions.

61 Claims, No Drawings

UTILIZATION OF A TRANSACYLATION REACTION BETWEEN AN ESTERIFIED POLYSACCHARIDE AND A POLYAMINATED OR POLYHYDROXYLATED SUBSTANCE FOR FABRICATING MICROPARTICLES, MICROPARTICLES THUS OBTAINED, METHODS AND COMPOSITIONS CONTAINING THEM

The present invention relates essentially to the use of a transacylation reaction between an esterified polysaccharide and a polyamino or polyhydroxylic substance for the manufacture of microparticles, to the microparticles, to the processes for their manufacture and to compositions in which they are present.

More precisely, the present invention relates essentially to the use of a transacylation reaction between on the one hand a polysaccharide carrying esterified carboxyl groups and on the other hand either a polyamino substance, in particular a protein, or a polyhydroxylic substance, in particular a polysaccharide, for the manufacture of microparticles, in particular microcapsules, to the microparticles produced in this way, to the processes for the manufacture of such microparticles, in particular microcapsules, and to the compositions in which they are present, such as cosmetic, pharmaceutical, food, enzyme, reagent or diagnostic compositions.

The development of biocompatible microparticles, in particular microcapsules, is of great interest especially in the fields of cosmetics, pharmaceuticals and foodstuffs. When charged with one or more active substances, these vesicles can in fact make it possible to mask an unpleasant taste or odor, to increase the stability of the encapsulated substances, to prevent their evaporation or to ensure their sustained release in situ. If the membrane is enteric, the microparticles, in particular the microcapsules, can also protect the active substance from degradation in the stomach or protect the gastric mucous membrane from an irritant effect.

Such microcapsules can be administered by a variety of routes, such as the oral route, application to the skin or mucous membranes, or the parenteral route.

Proteins and polysaccharides have been studied most among the various candidate materials. A variety of processes have thus been described for the preparation of microcapsules from proteins or polysaccharides or associations of proteins and polysaccharides. Some processes comprise a first stage involving emulsification of an aqueous solution of protein or polysaccharide within a hydrophobic phase, followed by a stage involving crosslinking with a difunctional agent such as acid dichlorides. Examples of documents which may be cited are FR-A-2 444 497 Mars or else FR-A-2 527 438 CNRS, in which interfacial crosslinking is applied to mixtures of proteins and polysaccharides.

To encapsulate hydrophobic liquids emulsified as the disperse phase in an aqueous solution of protein or polysaccharide, the existing processes generally consist either in heating the emulsion if the protein can be denatured by heat (for example the document US 3 137 631 Soloway), or in incorporating a crosslinking agent into the hydrophobic phase (the document US 4 138 362 Vassiliades).

Furthermore, the so-called complex coacervation processes are well known to those skilled in the art. They are applicable especially to aqueous solutions of a protein or a polyanionic substance, for example a polysaccharide carrying carboxyl groups. The substance to be encapsulated is dispersed in the aqueous phase either in the form of a solid, or in the form of droplets of an immiscible liquid. The principle is to acidify the aqueous solution so as to bring the pH to a value such that the protein is positively charged and forms with the polyanionic substance an electrically neutral complex, which deposits on the disperse phase to be encapsulated.

The processes which use difunctional crosslinking agents have the disadvantage of necessitating repeated washing of the resulting microcapsules in order to remove all the excess crosslinking agent. Moreover, the chemical crosslinking reaction substantially degrades the structure of proteins. For pharmaceutical applications, such degradations are to be avoided since they can be the cause of immunogenic properties of the microparticles. Likewise, if it is desired to preserve the specific biological properties of the protein used to prepare the microparticles, such as enzymic properties (immobilized enzyme) or oxygen transport properties (hemoglobin), attempts will be made to minimize any denaturation of the protein which could reduce its activity. This objective obviously cannot be achieved with processes which use the thermal denaturation of proteins, said processes having the further disadvantage of being inapplicable to thermolabile substances.

Complex coacervation processes are limited in their applications: they can only be applied to the encapsulation of water-insoluble substances or water-immiscible liquids. Moreover, as the wall of the microcapsules does not involve covalent bonds between the protein and the polyanionic substance, a consolidation treatment, for example a treatment with a crosslinking agent, is necessary.

Several patents (GB-A-768 309 Henkel; GB-A-962 483 AGFA) describe the formation of a thermostable solid film by the alkalization of an aqueous solution containing on the one hand a polysaccharide carrying esterified carboxyl groups, hereafter designated by "esterified polysaccharide", such as propylene glycol alginate (PGA), and on the other hand a diamine or a protein. The reaction between the ester groups of the esterified polysaccharide and the amino groups of the diamine or protein results in the formation of amide bonds. The reaction mechanism involves the migration of acyls in an alkaline medium in the O to N direction, the amino group causing a nucleophilic substitution of the ester with the release of propane-1,2-diol (McKay J. E., Stainsby G., Wilson E. L., Carbohydr. Polym., 5, 223–236, 1985; Stainsby G., Food Chem., 6, 3–14, 1970). This reaction is closely dependent on the pH of the aqueous phase: the system has to be rendered alkaline in a controlled manner and for a precise time, or else the network formed is quickly destroyed by hydrolysis of the glycosidic linkages in the polysaccharide.

The documents of the prior art also indicate the possibility of obtaining solid films by the alkalization of solutions containing both propylene glycol alginate (PGA) and a polyhydroxylic compound such as starch, carboxymethyl cellulose or polyvinyl alcohol (the document 1 135 856 BP). This phenomenon, which also arises to a certain extent with PGA on its own, is attributed to a transacylation (transesterification) reaction between the PGA and the polyhydroxylic derivative.

These phenomena have so far never been applied to emulsions.

If the conditions are based on those described in the literature, i.e. the use of an esterified polysaccharide such as PGA with a high degree of substitution (>50%), a pH of between 9.3 and 10.5 and an alkalization time of 15 min, followed by neutralization through the addition of an acid, and if an attempt is made to apply the reaction directly to an emulsion of an alkaline aqueous solution containing both PGA, on the one hand, and by a polyamino compound such as a protein or a polyhydroxylic compound such as a polysaccharide, on the other, said alkaline aqueous solution being used as the disperse phase within a hydrophobic phase, it is not possible to obtain microparticles or microcapsules for any concentration of PGA and polyamino or polyhydroxylic compound. The alkaline aqueous phase containing the two compounds in solution solidifies very rapidly if the pH is sufficiently high, making any emulsification in a hydrophobic phase impossible, whereas a stable film is not formed at lower pH values. It is therefore necessary to emulsify the neutral aqueous phase containing the two biopolymers as the disperse phase within a hydrophobic phase as the continuous phase, and then to initiate the transacylation reaction within the emulsion. However, the problem arises of carrying out this process in such a way that the alkaline agent added to the emulsion diffuses through the hydrophobic phase and right into the droplets of the aqueous disperse phase. The addition of an alkaline aqueous solution to the emulsion does not afford this result. The same problem arises with the neutralization of the medium by acidification at the end of the reaction, which cannot be effected by the addition of an acid aqueous solution.

Likewise, if an attempt is made to apply the phenomenon to an emulsion of a hydrophobic phase as the disperse phase in an aqueous phase as the continuous phase, consisting of an alkaline solution of PGA and a polyamino compound such as a protein or a polyhydroxylic compound such as a polysaccharide, microcapsules cannot be obtained for any concentration of PGA and polyamino or polyhydroxylic compound. The alkaline aqueous phase solidifies if the pH is sufficiently high, or else does not deposit a stable film on the dispersed hydrophobic droplets at lower pH values.

The document GB-A-962 483 AGFA describes a reaction (alginic acid esters), in particular glycol esters with amines such as hexamethylenediamine, proteins for the formation of a bonding agent for a photographic emulsion layer. This document does not relate to the technical field of the manufacture of microcapsules, which is a totally different technical field from that of photographic emulsion layers.

Likewise, the document GB-A-763 309 Henkel relates to a process for the production of alginic acid amides, and in particular of gel-forming amides of alginic acid, for effecting surface gelling and coating, an application which appears to be the essential application of alginic acid esters or derivatives.

The document GB-A-1 135 856 relates to a process for the modification of alkylene glycol alginates for the formation of suspending agents and binders and adhesives, in particular for binding powdered or granular materials, for the formation of a water-resistant surface coating and elastic jellies (page 2, line 121 to page 3, line 104) or in cosmetic products for utilizing this binding capacity. Therefore this document also does not relate in any way to the technical field of the manufacture of microcapsules.

One object of the present invention is to prepare stable microparticles, preferably microcapsules, from polyamino compounds, in particular proteins, or from polyhydroxylic compounds, in particular polysaccharides, at laboratory temperature, without a difunctional crosslinking agent, said microparticles containing either a hydrophilic phase or a hydrophobic phase, according to whether either an emulsion of a hydrophilic phase as the disperse phase in a hydrophobic liquid as the continuous phase, or an emulsion of a hydrophobic phase as the disperse phase in an aqueous liquid as the continuous phase, is initially prepared.

Another object of the present invention is to prepare microparticles, preferably microcapsules, from proteins, limiting the degradation of their structure so as to obtain an improved biocompatibility and so as to preserve a specific biological activity in the case where the protein possesses this activity.

Yet another object of the present invention is to solve the problem of the alkalization of the droplets of the neutral aqueous phase containing both an esterified polysaccharide such as PGA, on the one hand, and the polyhydroxylic or polyamino compound, on the other, once the droplets are dispersed within a hydrophobic phase in the form of an emulsion, and then the problem of their neutralization by acidification, at the end of the reaction, within the emulsion.

Another object of the present invention, in the case of an emulsion of a hydrophobic liquid as the disperse phase in an aqueous phase containing both the esterified polysaccharide, on the one hand, and the polyhydroxylic or polyamino compound, on the other, is to carry out a localized alkalization around the droplets of the hydrophobic phase and not in the entire volume of the aqueous continuous phase, so as to initiate the transacylation reaction selectively at the interface of the emulsion.

Yet another object of the present invention is to prepare microparticles, preferably microcapsules, from an esterified polysaccharide, on the one hand, and polyamino or polyhydroxylic compounds soluble in hydrophobic liquids, on the other, by producing separate solutions of the reactants in immiscible phases and by initiating the transacylation reaction at the interface of an emulsion at the desired moment, following the principles explained above.

Yet another object of the present invention is to solve the above mentioned technical problems by means of simple manufacturing processes which can be used on the industrial scale and which also make it possible to adjust the size of the microparticles, preferably microcapsules, in particular over a range of dimensions extending from less than 1 µm to 5000 µm.

According to the present invention, it has been discovered, totally unexpectedly, that the in situ alkalization of the aqueous droplets dispersed within a hydrophobic phase in the form of an emulsion can be effected in an extremely simple manner by the addition, to the emulsion, of a solution of an alkaline agent in an organic liquid miscible with the aqueous phase. The transacylation reaction can thus be initiated after the emulsification step. After the reaction, the neutralization is then effected in the same manner by the addition, to the reaction medium, of a solution of an acid in an organic liquid miscible with the aqueous phase. It is thus possible to isolate microscopic spheres consisting of a polyamino substance such as a protein, or a polyhydroxylic substance such as a polysaccharide, directly associated by covalent bonds with a polycarboxylic polysaccharide, no other reagent being added.

It has likewise been discovered, unexpectedly, that the addition, to a hydrophobic phase, of an alkaline agent dissolved in an organic liquid miscible with the aqueous phase permits, once this mixture has been emulsified as the disperse phase in a neutral aqueous phase containing both the esterified polysaccharide, on the one hand, and the polyhydroxylic or polyamino compound, on the other, a diffusion of alkaline ions to the interface, which is capable of initiating in situ the transacylation reaction and the formation of a membrane around the hydrophobic droplets, and that the microparticles, preferably microcapsules, which have thus been formed and then neutralized by the addition of a solution of an acid in a water-miscible organic liquid or in water can easily be separated from the continuous phase without a solidification problem.

Finally, it has been discovered that microparticles, preferably microcapsules, can be prepared by means of an interfacial transacylation reaction starting from an esterified polysaccharide such as PGA, dissolved in the aqueous phase, on the one hand, and a polyhydroxylic compound such as a cellulose derivative, or a polyamino compound such as hexamethylenediamine, dissolved in a hydrophobic phase, on the other. The aqueous phase can be used as the disperse phase or as the continuous phase. However, if the solution of esterified polysaccharide is rendered alkaline before the emulsification stage, hydrolysis reactions of the ester groups and transesterification reactions between polysaccharide chains will reduce the number of ester groups available for the reaction, which is unfavorable to the formation of the membrane and at the same time increases the viscosity of the aqueous phase, hindering the emulsification.

It will therefore be necessary to use a neutral aqueous solution of the esterified polysaccharide and, once the emulsion has been obtained in the presence of the hydrophobic phase, to initiate alkalization at the interface. It has been discovered that this problem can easily be solved using the processes described above. In fact, in the case where the aqueous phase is used as the disperse phase, it has been possible to verify that the in situ alkalization of the dispersed aqueous droplets can be effected in the same manner by the addition, to the emulsion, of a solution of an alkaline substance in an organic liquid miscible with the aqueous phase. The microparticles, preferably microcapsules, are then neutralized by the same process using a solution of an acid in an organic liquid miscible with the aqueous phase. Similarly, in the case where the hydrophobic phase is used as the disperse phase, it has been found that a diffusion of alkaline ions to the periphery of the dispersed droplets can very easily be achieved within the emulsion by the addition, to the hydrophobic phase, of a solution of an alkaline agent in an organic liquid miscible with the aqueous phase. An interfacial transacylation reaction is initiated in this way. The microparticles formed, preferably the microcapsules formed, are then neutralized by the addition, to the reaction medium, of a solution of an acid in an organic liquid miscible with the aqueous phase or in water.

It is on the basis of this discovery, totally unexpected to those skilled in the art, that the present invention has been carried out. The invention represents a decisive technical advance for those skilled in the art, taking into account the fact that the microparticles obtained, preferably the microcapsules obtained, which result from the formation of covalent bonds by the transacylation reaction, are perfectly stable even though they are made up only of biocompatible substances, to the exclusion of any difunctional crosslinking agent. Thus they may have numerous applications in various fields such as pharmacy, cosmetics and the food industry. The possibility of incorporating both hydrophobic substances and hydrophilic substances into the microparticles, preferably microcapsules, constitutes a further important advantage of the invention. Thus microparticles, preferably microcapsules, charged with oils such as essential oils, or with oily solutions of active substances, can be prepared just as easily as microparticles, preferably microcapsules, containing aqueous solutions or even suspensions or emulsions with an aqueous continuous phase. Moreover, the composition of the microparticles, preferably microcapsules, may be chosen for example so that digestion by proteases may or may not take place, by using a polyamine such as a protein or, respectively, a polyhydroxylic substance such as a polysaccharide to react with the esterified polysaccharide.

Finally, the controlled conditions of the process do not cause substantial denaturation of proteins, so said process can be applied to enzymes without suppressing their activity, which gives a novel type of immobilized enzymes.

Thus, according to a first feature, one subject of the present invention is the use of a transacylation reaction between a polysaccharide carrying esterified carboxyl groups and a polyamino substance, in particular a polysaccharide carrying amine groups, such as chitosan, or a protein, or a polyhydroxylic substance, in particular a polysaccharide, for the manufacture of microparticles, in particular microcapsules. These microparticles, in particular microcapsules, preferably contain an active principle for use in cosmetics, pharmaceuticals or foodstuffs, or a protein possessing a biological activity, such as an enzyme or hemoglobin.

According to a second feature, another subject of the present invention is microparticles, in particular microcapsules, characterized in that they have a wall consisting of the reaction product of a polysaccharide carrying esterified carboxyl groups and a polyamino substance such as a polysaccharide carrying amine groups, like chitosan, or a protein, or a polyhydroxylic substance such as a polysaccharide.

In one particular reaction variant, these microparticles, in particular these microcapsules, have a wall consisting of the reaction product of a polysaccharide carrying esterified carboxyl groups and a polyamino substance such as a polysaccharide carrying amine groups, like chitosan, or a protein, thereby having covalent amide bonds involving the amine groups of the polyamine and the carboxyl groups of the esterified polysaccharide. Advantageously, the proportions of the esterified polysaccharide relative to the polyamine such as a protein, or a polysaccharide such as chitosan, can vary from 0.4% to 60% by weight. In the particular case where a diamine is used as the polyamine, a particular proportion of this diamine relative to the esterified polysaccharide can be more precisely between 5 and 30% by weight.

In another variant, the microparticles, in particular microcapsules, are characterized in that they have a wall consisting of the reaction product of a polysaccharide carrying esterified carboxyl groups and a polyhydroxylic substance, for example a polysaccharide, by way of covalent ester bonds involving the carboxyl groups of the esterified polysaccharide and the hydroxyl groups of the polyhydroxylic compound. Advantageously, the proportions of esterified polysaccharide relative to the polyhydroxylic compounds can vary from 5% to 300% by weight.

In one particularly advantageous embodiment, these microparticles, in particular these microcapsules, contain an active principle for use in cosmetics, pharmaceuticals or foodstuffs, or a protein with biological activity, such as an enzyme or hemoglobin, or else bubbles of a gas such as air.

According to a third feature, the present invention relates to a process for the manufacture of microparticles, in particular microcapsules, characterized by the following successive steps:

a) a neutral aqueous solution is prepared which contains on the one hand a polysaccharide carrying esterified carboxyl groups and on the other hand either a polyamino substance, for example a polysaccharide carrying amine groups, such as chitosan, or a protein, or a polyhydroxylic substance, for example a polysaccharide;

b) a hydrophobic liquid is provided in which the esterified polysaccharide and the polyamino or polyhydroxylic substance are essentially insoluble;

c) the hydrophobic liquid and the aqueous solution are mixed to form an emulsion;

d) a solution of an alkaline substance in an organic liquid miscible with the aqueous phase is added to the emulsion; and e) after a predetermined period of time required to effect a transesterification reaction, thereby forming microparticles, in particular microcapsules, the emulsion is neutralized preferably by the addition, to the emulsion, of a solution of an acid substance in an organic liquid miscible with the aqueous phase, which neutralizes and stabilizes the microparticles formed, in particular the microcapsules formed.

In one variant, the emulsion formed is an emulsion of the aqueous solution as the disperse phase in the hydrophobic liquid as the continuous phase.

In another embodiment, the hydrophobic liquid forms the disperse phase, in which case a solution of an alkaline substance in an organic liquid miscible with the aqueous phase is added to the hydrophobic liquid, after which this hydrophobic phase is dispersed in the above mentioned neutral aqueous solution as the continuous phase so as to form the above mentioned emulsion, which allows the transacylation reaction to develop on the surface of the dispersed droplets by diffusion of the alkaline ions to the interface.

Thus, according to a fourth feature, the present invention relates to a process for the manufacture of microparticles, in particular microcapsules, characterized by the following successive steps:

a) a neutral aqueous solution of a polysaccharide carrying esterified carboxyl groups is prepared;

b) a hydrophobic solution of a polyamino substance, for example a polysaccharide carrying amine groups, such as chitosan, or a protein or a diamine, or of a polyhydroxylic substance, for example a polysaccharide or hydroxypropyl cellulose, is prepared in a hydrophobic liquid in which the esterified polysaccharide is essentially insoluble, after which a solution of an alkaline agent in an organic liquid miscible with the aqueous phase is added to said hydrophobic solution;

c) an emulsion of this mixture as the disperse phase in the neutral aqueous solution of the esterified polysaccharide as the continuous phase is formed and the transacylation reaction is allowed to develop on the surface of the dispersed droplets by diffusion of the alkaline ions to the interface; and d) after a predetermined reaction time, a solution of an acid substance in an organic liquid miscible with the aqueous phase or in water is added to the reaction medium so as to neutralize and hence stabilize the microparticles, in particular the microcapsules.

In another embodiment, the present invention further relates to a process for the manufacture of microparticles, in particular microcapsules, characterized by the following successive steps:

a) a neutral aqueous solution of a polysaccharide carrying esterified carboxyl groups is prepared;

b) a solution of a polyamino substance or a polyhydroxylic substance is prepared in a hydrophobic liquid in which the esterified polysaccharide is essentially insoluble;

c) an emulsion of the aqueous solution as the disperse phase in the hydrophobic liquid as the continuous phase is formed;

d) a solution of an alkaline substance in an organic liquid miscible with the aqueous phase is added to the emulsion so as to initiate the interfacial transacylation reaction and hence form microparticles, in particular microcapsules; and e) after the reaction, a solution of an acid substance in an organic liquid miscible with the aqueous phase is added to the emulsion so as to neutralize and hence stabilize the microparticles, in particular the microcapsules.

Advantageously, the above mentioned process can also comprise a complementary step for separation of the microparticles, in particular microcapsules, by any appropriate means, especially by natural decantation after one or more washes have optionally been carried out.

According to one advantageous characteristic of the manufacturing processes according to the invention, once they have been separated from the reaction medium, the microparticles, in particular the microcapsules, can be placed in an aqueous or alcoholic solution of lime so as to initiate a reaction between the functional groups of the esterified polysaccharide and calcium ions. It is well known that such a reaction creates a network structure capable of behaving like a matrix system. The particular structure of the microparticles obtained, in particular the microcapsules obtained, is thus capable of permitting a more effective trapping and/or a slower diffusion of the substances encapsulated or trapped in the matrix.

According to one advantageous characteristic of the invention, which is of course applicable to any one of the features of the invention, the substance or the polyamino compound can be a protein which may or may not be partially hydrolyzed and may or may not be grafted with a long hydrocarbon chain. Long hydrocarbon chain is understood as meaning chains containing from 10 to 30 carbon atoms. The substance or the polyamino compound can also be selected from hydrophilic proteins, i.e. water-soluble or water-dispersible proteins, containing free amine groups.

It is not essential for the protein materials used in the reaction to be pure proteins. They can be used in the form of natural or unnatural mixtures containing hydrophilic proteins, for example milk or mixtures of atelocollagen and glycosaminoglycans.

Examples of proteins which can be used in the invention and which satisfy the conditions of being hydrophilic, or else which can be treated so as to become hydrophilic, are albumins such as serum albumin, ovalbumin and alpha-lactalbumin, globulins, fibrinogen, casein, glutelins, which will preferably have been degraded, solubilized scleroproteins, collagen, atelocollagen, gelatin, hemoglobin and enzymes such as catalase.

Examples which may be mentioned of mixtures containing hydrophilic proteins are whole milk or totally or partially skimmed milk, powdered milk, condensed milk, whey proteins, whole egg, egg yolk and mixtures of atelocollagen and glycosaminoglycans.

Within the framework of the invention, the polyamino substance can be a polysaccharide carrying amine groups, such as chitosan, a diamine such as an alkylenediamine preferably having from 2 to 6 carbon atoms, like ethylenediamine, trimethylenediamine, tetramethylenediamine, pentamethylenediamine or hexamethylenediamine, a diamine comprising an aromatic ring, such as m-phenylenediamine or p-phenylenediamine, an alkylenepolyamine such as tetraethylenepentamine, or an amine containing a ring nitrogen atom, such as piperazine, these examples being cited by way of illustration and without implying a limitation.

According to another advantageous characteristic of the invention, applicable to any one of the features of the invention, the esterified polysaccharide is a hydrophilic polysaccharide carrying a large number of carboxyl groups which are esterified in a proportion of at least 50%, either naturally or by chemical modification. According to a preferred characteristic, the polysaccharide ester is selected from propylene glycol alginate and pectins.

According to another advantageous characteristic of the processes according to the invention, the concentration of polysaccharide ester in the aqueous phase is between 0.4% and 5% w/v, preferably from 0.7 to 2% and particularly preferably about 1%.

According to another advantageous characteristic of the processes according to the invention, the concentration of protein or polyamine in the aqueous phase is between 0.2% and 35%.

According to another advantageous characteristic of the invention, applicable to all the features of the invention, the polyhydroxylic substance capable of reacting with the esterified polysaccharide is a polysaccharide or polysaccharide derivative such as starch or partially hydrolyzed starch, hydroxyethyl starch, carboxymethyl starch, sodium alginate, guar gum, gum arabic, gum tragacanth or various cellulose derivatives such as hydroxypropyl cellulose, carboxymethyl cellulose, ethyl cellulose, hydroxypropyl methyl cellulose or hydroxyethyl cellulose.

According to another advantageous characteristic of the invention, applicable to all the features of the invention, the polyhydroxylic substance capable of reacting with the esterified polysaccharide is a polyalcohol such as polyvinyl alcohol, an alkylene glycol, in particular a $C_2$–$C_6$-alkylene glycol, for example ethylene glycol, butane-1,4-diol, hexamethylene glycol or glycerol, these polyalcohols being cited by way of illustration and without implying a limitation.

The aqueous phase can consist either of pure water or of a buffer with a pH of between 5.9 and 8, preferably of between 6.8 and 7.5.

Any solvent described in the above documents can be used as the hydrophobic liquid in which the protein or polyamine and the polysaccharide ester are insoluble. It is preferable to use chloroform, dichloromethane, cyclohexane, paraffin oil or isopropyl myristate, or else natural or synthetic glycerides, either pure or as mixtures, vegetable oils, for example groundnut oil, olive oil or colza oil, or fatty acid esters of various alcohols, for example methyl or ethyl oleates, either by themselves or as mixtures.

According to another advantageous characteristic of the processes according to the invention, the emulsion is produced in the presence of a surfactant. When the aqueous phase is used as the disperse phase, it will be possible for example to use a sorbitan ester or a lecithin incorporated in the hydrophobic phase. When the hydrophobic phase is used as the disperse phase, it will be possible for example to use polysorbate incorporated in the aqueous phase. However, a surfactant is not necessary for the processes according to the invention to take place satisfactorily and it can be omitted.

According to another advantageous characteristic of the processes according to the invention, the alkaline organic liquid miscible with the aqueous phase is a solution of sodium hydroxide or potassium hydroxide in an alcohol such as methanol or ethanol, used pure or containing 5 to 10% of water, or else a polyol such as glycerol or a polyethylene glycol. According to a preferred characteristic, the solution contains between 0.5 and 2% w/v of sodium hydroxide in 95% ethanol and particularly preferably a sodium hydroxide concentration of about 2%.

According to another advantageous characteristic of the processes according to the invention, the time for which an alkaline pH is maintained to enable the transacylation reaction to develop is between 5 min and 1 h, preferably between 5 min and 30 min and particularly preferably 15 min.

According to another advantageous characteristic of the processes according to the invention, the acid organic liquid miscible with the aqueous phase is a solution of a monocarboxylic or polycarboxylic organic acid which may or may not carry alcohol groups, such as acetic acid, citric acid, lactic acid, tartaric acid, succinic acid or malic acid, or a mineral acid such as hydrochloric acid, in an alcohol such as methanol or ethanol, used pure or containing 5 to 10% of water, or else in a polyol such as glycerol or a polyethylene glycol. According to a preferred characteristic, the acid solution consists of 95% ethanol containing between 1 and 10% (v/v) of acetic acid, preferably between 7 and 8%.

According to another advantageous characteristic of the processes according to the invention, the neutralization time of the microcapsules, i.e. the agitation time required after addition of the acid solution to the reaction medium, is between 5 min and 1 h, preferably between 5 min and 30 min and particularly preferably 15 min.

Depending on the type of emulsion produced and the chosen protocol, one or more active principles in the form of a solution, suspension or emulsion, in particular one or more substances of interest in cosmetics, pharmaceuticals or foodstuffs, can be introduced into the aqueous phase or into the oily phase.

It is also possible to trap a foam inside the microparticles, in particular the microcapsules. Thus, for example, bubbles of a gas such as air can be incorporated into an aqueous solution of protein and esterified polysaccharide by subjecting said solution to very vigorous agitation. The process of the invention is then applied to the foam by using it as the aqueous disperse phase within a hydrophobic phase. After drying, the microparticles, in particular the microcapsules, contain a multitude of trapped bubbles of a gas such as air. Such microparticles, in particular microcapsules, have an indicated use in methods of medical diagnostics by echography.

If a protein possessing a biological activity, such as an enzyme or hemoglobin, is used to react with the esterified polysaccharide, the microcapsules obtained according to the invention can constitute an immobilized form which is easy to use, especially in the fields of biotechnology, bioreagents or therapeutics. Thus, for example, in the field of therapeutics, the immobilized or encapsulated enzymes have valuable indicated uses in substitutive therapy, by oral administration in digestive enzyme insufficiencies or by parenteral administration for the treatment of diseases associated with congenital enzyme deficiencies. They are also useful within the framework of the treatment of certain tumors, or locally for the treatment of wounds and ulcers, or even in extracorporeal blood purification systems. The effect of immobilization is to protect the enzyme against various inactivating agents, to slow down the attack thereon by proteases and to reduce its immunogenicity. As far as hemoglobin is concerned, microcapsules which have been prepared from this protein and have retained its oxyphoric properties have applications as "artificial red blood corpuscles", or else in biotechnology for the oxygenation of bioreactors.

Finally, according to a fifth feature, the present invention further relates to a composition such as a cosmetic composition, a pharmaceutical composition, a food composition or an enzyme composition, characterized in that it comprises microparticles, in particular microcapsules, which have a wall consisting of the reaction product of a polyamino or polyhydroxylic substance with a polysaccharide carrying esterified carboxyl groups, either by way of amide bonds involving the amine groups of the protein or polyamine, on the one hand, and the carboxyl groups of the polysaccharide, on the other, or by way of ester bonds involving the hydroxyl groups of the polyhydroxylic substance, on the one hand, and the carboxyl groups of the esterified polysaccharide, on the other.

Diverse variants of this composition clearly result from the diverse advantageous characteristics or variants of the processes of the invention described according to any one of the other features above, and from the following description referring to numerous Examples of the invention, which are given by way of illustration and therefore have a general scope.

Thus, for carrying out the invention, it is clear that if a manufacturing process is used in which an aqueous solution containing a polysaccharide carrying esterified carboxyl group and a polyamino substance or a polyhydroxylic substance is prepared, this substance must be chosen for its solubility capacity in aqueous solution. Likewise, if within the framework of a process of the invention a hydrophobic solution of a polyamino or polyhydroxylic substance is prepared, said substance is chosen for its solubility capacity in hydrophobic solution, as is well known to those skilled in the art.

Other objects, characteristics and advantages of the invention will become clearly apparent from the following explanatory description referring to several Examples of the invention, which are given simply by way of illustration and cannot therefore in any way limit the scope of the invention.

EXAMPLE 1

According to the Invention

Manufacture of microparticles of mean diameter 150 µm from human serum albumin (HSA) and propylene glycol alginate (PGA)

a) Preparation of the aqueous phase

A solution in distilled water containing 20% of HSA (Centre de Transfusion Sanguine, Strasbourg) and 1% of a PGA having a degree of esterification of between 80 and 85% (Kelcoloid S®, KELCO International) is prepared by magnetic agitation for 10 min at room temperature.

b) Emulsification 6 ml of this aqueous phase are emulsified as the disperse phase, by mechanical agitation for 5 min at 2000 rpm, in 40 ml of isopropyl myristate containing 2% v/v of Span 85® as the continuous phase.

c) Alkalization 2 ml of a 2% w/v solution of sodium hydroxide in 95% ethanol are added to the emulsion, with agitation, and the transacylation reaction is allowed to develop for 15 min to produce microparticles.

d) Acidification 2 ml of a 7.6% v/v solution of acetic acid in 95% ethanol are added to the reaction medium, with agitation. Agitation is maintained for a further 15 min to permit the neutralization of the microparticles formed.

e) Washes

The microparticles are separated off by centrifugation and subsequently washed by resuspension in 95% ethanol containing 2% of Tween 20®, then in 95% ethanol and then in distilled water.

The microparticles can then be frozen and lyophilized.

This gives transparent spheres with a mean size of 150 µm. After lyophilization, rehydration of the powder obtained shows that the microparticles are intact and resume their spherical shape.

Stability tests in various media containing or not containing proteases

In test tubes, 25 mg samples of lyophilized microparticles are rehydrated by the addition of 1 ml of distilled water, after which 7.5 ml of the following different media are added:

distilled water a solution of acid pH (1.2) to which pepsin (artificial gastric medium, USP XXI) may or may not have been added a solution of slightly alkaline pH (7.5) to which trypsin (0.25% w/v) may or may not have been added.

The tubes are incubated at 37° C. The stability of the microparticles is studied by microscopic examination. The lysis time is the time after which all the microparticles have disappeared from the medium.

Results: The microparticles prepared according to Example 1 are stable for more than 3 d in distilled water and in the solutions of pH 1.2 or pH 7.5. They are degraded by proteases: in 15 min by pepsin and in 25 min by trypsin.

EXAMPLE 2

According to the Invention

Manufacture of microparticles of mean diameter 15 µm from HSA and PGA

The protocol described in Example 1 is repeated, replacing the isopropyl myristate with fluid paraffin oil.

This gives spherical microparticles with a mean diameter close to 15 µm. This Example shows that, for given emulsification conditions, the diameter of the microparticles can be adjusted by the choice of continuous phase.

EXAMPLE 3

According to the Invention

Manufacture of microparticles of mean diameter 200 µm from ovalbumin and PGA, containing a water soluble dye The protocol described in Example 1 is repeated, replacing the human serum albumin with ovalbumin (LABOSI), used at the same concentration (20%), and dissolving patent blue V at a concentration of 1% in the aqueous phase. The washing protocol is modified: the microparticles are washed with cyclohexane. They are then freed of solvent by evaporation under vacuum, frozen and lyophilized.

This gives blue-colored spherical microparticles of mean diameter 200 µm. They withstand incubation in distilled water, in a solution of pH 1.2 or in a solution of pH 7.5 for more than 3 d. The microparticles are resistant to pepsin for at least 24 h and are lyzed by trypsin in 3 h.

Stability test in distilled water at 45° C.

The microcapsules which have now been obtained in suspension in distilled water are centrifuged and freed of supernatant. 1 g of the residue of microcapsules dried in this way is taken and this sample is suspended in 50 ml of sterile distilled water. The flask is stoppered and then placed in an oven at 45° C. It is observed that the microcapsules have remained intact after a residence time of 2½ months in the oven.

EXAMPLE 4

According to the Invention

Manufacture of microparticles of mean diameter 75 µm from ovalbumin and PGA

The protocol described in Example 3 is repeated, replacing the isopropyl myristate with chloroform and using polyethylene glycol 200 instead of 95% ethanol to prepare the sodium hydroxide and acetic acid solutions.

This gives microparticles of mean diameter 75

EXAMPLE 5

According to the Invention

Manufacture of microparticles of mean diameter 250 µm from hemoglobin and PGA

The protocol described in Example 1 is repeated, replacing the human serum albumin with ovine hemoglobin (SIGMA), used at a concentration of 15% w/v.

This gives bright red-colored spherical microparticles of mean diameter 250 µm, which can be lyophilized. These microparticles are destroyed by pepsin in 10 min and by trypsin in 3 h 30 min.

Stability test in distilled water at 45° C.

Under the same stability test conditions as those described in Example 3, it is observed that the microcapsules are intact after a residence time of 2½ months in an oven at 45° C., in the form of an aqueous suspension.

EXAMPLE 6

According to the Invention

Manufacture of microparticles of mean diameter 50 µm from hemoglobin and PGA

The protocol described in Example 5 is repeated, replacing the isopropyl myristate with chloroform.

This gives red microparticles of mean diameter 50 µm.

This is a further Example showing that, for given emulsification conditions, the diameter of the microparticles can be adjusted by the choice of hydrophobic continuous phase.

EXAMPLE 7

According to the Invention

Manufacture of microparticles of mean diameter 250 µm from fibrinogen and PGA

The protocol described in Example 1 is repeated, replacing the human serum albumin with bovine fibrinogen (SIGMA), used at a concentration of 6% w/v.

This gives microparticles of mean diameter 250 µm and of granular content, which can be lyophilized. These microparticles are resistant to pepsin for more than 24 h, whereas they are lyzed by trypsin in 3 h.

Stability test in distilled water at 45° C.

Under the stability test conditions described in Example 3, it is observed that the microcapsules are intact after a residence time of 2½ months in an oven at 45° C., in the form of an aqueous suspension.

EXAMPLE 8

According to the Invention

Manufacture of microparticles of catalase immobilized by PGA

The protocol described in Example 1 is repeated, replacing the human serum albumin with bovine liver catalase (C-10 from SIGMA), used at a concentration of 20% w/v.

This gives spherical microparticles of mean diameter 75 µm, which produce an easily rehydratable powder after lyophilization.

A large volume of gas is instantaneously evolved in the form of multiple bubbles when a pinch of this powder is brought into contact with 110 volume hydrogen peroxide.

Determination of the catalase activity (method of Feinstein, J. Biol. Chem., 1949, 180, p. 1197)

A 5 mg sample of lyophilized microparticles is rehydrated by the addition of 1 ml of phosphate buffer of pH 7 and magnetic agitation for 5 min at room temperature (20° C). 3 ml of a solution of sodium perborate titrated beforehand (against a 0.005M solution of $KMnO_4$), containing 88.46 mmol/l of $H_2O_2$, are added. The reaction is stopped after 30 s by the addition of 3 ml of 1M $H_2SO_4$. 1 ml of 20% trichloroacetic acid is added to the medium, which is filtered on a 0.22 µm filter. Using a 0.005M solution of $KMnO_4$, the residual $H_2O_2$ is determined on an aliquot of the filtrate to which a drop of 1% $MnCl_2$ has been added.

Results (mean of 3 tests):

After 30 s, only 34.17 µmol of substrate out of the 265.37 µmol initially present remain in the medium.

Tests performed in parallel with pure catalase under the same conditions indicate that, to observe an activity comparable to that of 5 mg of microparticles, it is necessary to use 1 ml of a catalase solution containing 5 mg/40 ml (residual substrate after 30 s, mean of 3 tests: 37.5 µmol).

Thus the 5 mg of lyophilized microparticles, which actually correspond to 4.762 mg of catalase used in the preparation, have the same activity as 0.125 mg of pure catalase which has not undergone lyophilization. These results demonstrate that the process for the preparation of microparticles according to the invention makes it possible to obtain microparticles having a valuable enzymic activity.

EXAMPLE 9

According to the Invention

If the protocol for the manufacture of microparticles described in Example 8 is applied, except that the solution of sodium hydroxide in 95% ethanol is replaced with a solution of sodium hydroxide in polyethylene glycol 200 (PEG 200) at the same concentration, and the solution of acetic acid in 95% ethanol is replaced with a solution of acetic acid in PEG 200 at the same concentration, stable microparticles (30 µm) are again obtained. If the catalase activity of a 5 mg sample of these lyophilized microparticles is determined under the conditions described in Example 8, it is found that a single drop of 0.005M $KMnO_4$ is sufficient to color the contents of the volumetric flask: all the $H_2O_2$ has therefore been decomposed in 30 s.

Thus, if the solutions of the alkaline and acid agents are prepared with a PEG instead of ethanol, the denaturation of the enzyme is limited, enabling a greater part of the enzymic activity to be preserved.

EXAMPLE 10

According to the Invention

Manufacture of microparticles from gelatin and PGA

Preparation of the aqueous phase: 8 ml of an aqueous solution of type B gelatin, bloom 150, at a concentration of 10% and PGA at a concentration of 1% are prepared at a temperature of 40° C.

Emulsification: In a thermostated vessel at 40° C., 6 ml of this aqueous phase are emulsified in 40 ml of isopropyl myristate containing 2% of Span 85 and preheated to a temperature of 40° C (agitation speed: 2000 rpm).

Alkalization, neutralization and washes are then effected as described in Example 1. The microparticles appear as spheres of mean diameter 1 mm. After lyophilization, they give a white powder which is readily rehydratable.

EXAMPLE 11

According to the Invention

Manufacture of microparticles from atelocollagen, chondroitin sulfate and PGA

Preparation of the aqueous phase: PGA is added at a concentration of 0.7% to a solution containing 1.6% of atelocollagen and 0.6% of chondroitin sulfate in a phosphate buffer of pH 7.4. The protocol described in Example 1 is then applied to this aqueous solution.

Microparticles of mean diameter 600 µm are obtained.

EXAMPLE 12

According to the Invention

Manufacture of microparticles from atelocollagen chondroitin sulfate and PGA with subsequent $CaCl_2$ treatment The protocol described in Example 11 is repeated, 40 ml of 95% ethanol containing 2% of Tween 20 and 2% of $CaCl_2$ being added 15 min after the addition of the acid alcoholic solution. Agitation is continued for 15 min and the microparticles are then separated off by centrifugation and washed as described in Example 1.

This gives microparticles of mean diameter 300 µm and of granular content.

EXAMPLE 13

According to the Invention

Manufacture of microparticles from atelocollagen, chondroitin sulfate and PGA, containing air bubbles Preparation of the aqueous phase: PGA is added at a concentration of 0.7% to a solution containing 1.6% of atelocollagen and 0.6% of chondroitin sulfate in a phosphate buffer of pH 7.4 and the resulting solution is mixed by mechanical agitation at low speed (300 rpm) for 6 min.

Incorporation of air: To incorporate air bubbles into the aqueous phase, the agitation speed is increased to 5000 rpm and maintained at this value for 3 min to produce a foam.

Emulsification: 24 ml of the foam are emulsified as the disperse phase in 80 ml of isopropyl myristate containing 2% of Span 85, the agitation speed being 2000 rpm.

The alkalization and acidification operations are then carried out as described in Example 1, except that 8 ml of the alkaline and acid alcoholic solutions are used. The washes are effected as described in Example 1.

This gives translucent beige-colored microparticles of mean diameter 600 µm, containing visible air bubbles (about 20 to 30 per microparticle) and floating on the surface of the water. After lyophilization and rehydration, the microparticles appear charged with air bubbles under the microscope. They float on the water for at least 9 h. The microparticles have formed a sediment after 48 h. The air bubbles are no longer present in the microparticles, the latter retaining, in the space occupied by the bubbles, smooth circular cavities visible under an interference phase-contrast optical microscope.

EXAMPLE 14

According to the Invention

Manufacture of microparticles from whole milk and PGA, containing an insoluble pigment in suspension Preparation of the aqueous phase: 60 mg of PGA are dissolved in 6 ml of liquid whole milk by agitation. 60 mg of the insoluble red dye RED DC 30 are dispersed in this solution by agitation.

The protocol described in Example 1 is then repeated using 6 ml of the above solution as the aqueous phase.

This gives red-colored microparticles of mean diameter 300 µm. The microparticles are intact after lyophilization.

EXAMPLE 15

According to the Invention

Manufacture of microparticles from skimmed milk powder and PGA, containing olive oil emulsified in the aqueous phase Preparation of the aqueous phase: 4 g of skimmed milk powder are dissolved in 16 ml of distilled water by agitation for 3 min. 160 mg of PGA are then dissolved in this solution by agitation for 6 min.

3 ml of olive oil are emulsified as the disperse phase in the above solution as the continuous phase by agitation at 5000 rpm.

The protocol described in Example 1 is then repeated using 12 ml of the above emulsion as the aqueous phase and doubling all the volumes of the various reagents. The microparticles are washed with distilled water to which 2% of Tween 20 has been added, and then with distilled water.

After washing, very spherical microparticles of mean diameter 400 µm are obtained. Microscopic examination shows a granular content within which the oil droplets are discerned in the form of very small refringent spheres. The microparticles are intact after lyophilization.

EXAMPLE 16

According to the Invention

Manufacture of microparticles from skimmed milk powder and PGA, containing essential oil of peppermint emulsified in the aqueous phase Preparation of the aqueous phase: 1.6 g of skimmed milk powder are dissolved in 8 ml of distilled water by agitation for 3 min. 80 mg of PGA are then dissolved in this solution by agitation for 6 min.

1 ml of essential oil of peppermint is emulsified as the disperse phase in the above solution as the continuous phase by agitation at 5000 rpm.

The protocol described in Example 1 is then repeated using 6 ml of the above emulsion as the aqueous phase. Alkalization is carried out by the addition of 2 ml of a 2.8% solution of potassium hydroxide in 95% ethanol and acidification is carried out by the addition of 2 ml of a 28.1% solution of citric acid monohydrate in 95% ethanol. The microparticles are washed as described in Example 15.

This gives very spherical microparticles of mean diameter 150 µm. Microscopic examination shows a granular content within which the droplets of essential oil are discerned in the form of very small refringent spheres.

EXAMPLE 17

According to the Invention

Manufacture of microparticles from a whey protein concentrate and PGA

Preparation of the aqueous phase: 160 mg of PGA and 3.2 g of whey protein concentrate (Prosobel S65E, Bel Industries) are dissolved in 16 ml of distilled water.

The protocol described in Example 1 is then repeated using 12 ml of the above solution as the aqueous phase and doubling all the volumes of the various reagents.

This gives spherical microparticles of mean diameter 500 μm and of granular content, which are intact after lyophilization.

EXAMPLE 18

According to the Invention

Manufacture of microparticles from hexamethylenediamine (HMD, Fluka) and PGA

Preparation of the aqueous phase: 16 mg of HMD are dissolved in 4 ml of phosphate buffer of pH 5.9. 200 mg of PGA are separately dissolved in 5 ml of phosphate buffer of pH 5.9. 4 ml of the HMD solution are mixed with 4 ml of the PGA solution by agitation for 1 min.

The protocol described in Example 1 is then repeated using 6 ml of the above solution as the aqueous phase and replacing the isopropyl myristate with methylene chloride.

This gives transparent microparticles of mean diameter 400 μm, which are intact after lyophilization. They are resistant to both trypsin and pepsin for more than 24 h.

EXAMPLE 19

According to the Invention

Manufacture of microparticles from ovalbumin and pectin

Preparation of the aqueous phase: 240 mg of apple pectin (FLUKA, esterification: 70 to 75%) and 800 mg of ovalbumin are dissolved in 8 ml of distilled water.

The protocol described in Example 1 is then applied using 6 ml of the above solution, replacing the isopropyl myristate with fluid paraffin oil and doubling the volumes of the alkaline and acid solutions.

This gives microparticles of mean size 200 μm and of granular content.

EXAMPLE 20

According to the Invention

Manufacture of microparticles from milk powder and pectin

Preparation of the aqueous phase: 240 mg of apple pectin and 800 mg of GLORIA skimmed milk powder are dissolved in 8 ml of distilled water.

The protocol described in Example 1 is then applied using 6 ml of the above solution, replacing the isopropyl myristate with fluid paraffin oil and doubling the volumes of the alkaline and acid solutions. This gives spherical microparticles with a size of between 2 μm and 300 μm, which can be lyophilized.

EXAMPLE 21

According to the Invention

Manufacture of microparticles from polyvinyl alcohol (PVA) and PGA

Preparation of the aqueous phase: 80 mg of PVA (MERCK, degree of hydrolysis: 98%, molecular weight: 72,000) and 320 mg of PGA are dissolved at 40° C. in 8 ml of distilled water.

The protocol described in Example 1 is then applied using 6 ml of the above solution and replacing the isopropyl myristate with fluid paraffin oil.

This gives spherical microparticles of mean size 1.2 mm.

EXAMPLE 22

According to the Invention

Manufacture of microparticles from hydroxyethyl starch (HES) and PGA

Preparation of the aqueous phase: 1.472 g of Plasmastéril (Frésénius A. G.), corresponding to 1.28 g of HES, and 320 mg of PGA are dissolved in 8 ml of distilled water.

The protocol described in Example 1 is then applied using 6 ml of the above solution and replacing the isopropyl myristate with fluid paraffin oil.

This gives spherical microparticles of mean size 600 μm.

EXAMPLE 23

According to the Invention

Manufacture of microparticles from carboxymethyl cellulose and PGA

Preparation of the aqueous phase: 80 mg of CMC (CMC 7 LF, degree of substitution: 0.7, HERCULES) and 320 mg of PGA are dissolved in 8 ml of distilled water by magnetic agitation for 15 min at 40° C.

The protocol described in Example 1 is then applied using 6 ml of the above solution.

This gives granular microparticles of mean size 1.8 mm.

EXAMPLE 24

According to the Invention

Manufacture of microcapsules with an aqueous internal phase from hydroxypropyl cellulose in solution in a hydrophobic liquid and PGA in aqueous solution Preparation of the aqueous phase: 80 mg of PGA are dissolved in 4 ml of distilled water.

Preparation of the hydrophobic phase: 300 mg of hydroxypropyl cellulose (Klucel EF, AQUALON) are dissolved in 20 ml of chloroform.

Emulsification: 3 ml of the aqueous phase are emulsified as the disperse phase in 20 ml of the hydrophobic phase by agitation at 2000 rpm for 5 min.

Alkalization and acidification are then carried out as described in Example 1, except that 1 ml of alcoholic sodium hydroxide solution and 1 ml of alcoholic acetic acid solution are used.

The washes are effected as described in Example 1.

This gives spherical microcapsules of mean size 70 μm. After lyophilization, the microcapsules are intact and rehydrate rapidly to resume their spherical shape.

EXAMPLE 25

According to the Invention

Manufacture of microcapsules with a hydrophobic internal phase from hydroxypropyl cellulose in solution in a hydrophobic liquid and PGA in aqueous solution Preparation of the aqueous phase: 800 mg of PGA are dissolved in 40 ml of distilled water.

Preparation of the hydrophobic phase: 2 ml of a 2% solution of sodium hydroxide in 95% ethanol are added to 6 ml of chloroform. 160 mg of hydroxypropyl cellulose (Klucel EF, AQUALON) are dissolved in this mixture.

Emulsification: 6 ml of the hydrophobic phase are emulsified as the disperse phase in 40 ml of the aqueous phase by agitation at 2000 rpm.

After 15 min, 2 ml of the acid alcoholic solution prepared as described in Example 1 are added. After a further period of 15 min, the microcapsules are centrifuged and washed as described in Example 15.

This gives spherical microcapsules of mean size 10 µm.

EXAMPLE 26

According to the Invention

Manufacture of microcapsules with an aqueous internal phase from hexamethylenediamine in solution in a hydrophobic liquid and PGA in aqueous solution Preparation of the aqueous phase: 160 mg of PGA are dissolved in 8 ml of distilled water.

Preparation of the hydrophobic phase: 80 mg of hexamethylenediamine (FLUKA) are dissolved in 40 ml of cyclohexane.

Emulsification: 6 ml of the aqueous phase are emulsified as the disperse phase in 40 ml of the hydrophobic phase by agitation at 2000 rpm for 5 min.

Alkalization is then carried out as described in Example 1. After 15 min, acidification is carried out by the addition of 1 ml of 95% ethanol containing 28.3% v/v ml of acetic acid. The washes are effected as described in Example 1.

This gives spherical microcapsules of mean size 5 µm.

EXAMPLE 27

According to the Invention

Manufacture of microcapsules with an oily internal phase from hexamethylenediamine in solution in a hydrophobic liquid and PGA in aqueous solution Preparation of the aqueous phase: 800 mg of PGA are dissolved in 40 ml of distilled water.

Preparation of the hydrophobic phase: 16 mg of hexamethylenediamine are dissolved in 6 ml of cyclohexane to which 2 ml of 95% ethanol containing 2% of sodium hydroxide have been added.

Emulsification: 6 ml of the organic phase are emulsified as the disperse phase in 40 ml of the aqueous phase by agitation at 2000 rpm.

After 15 min, acidification and subsequent washes are effected as described in Example 25.

This gives microcapsules of mean size 50 µm.

EXAMPLE 28

According to the Invention

Manufacture of microcapsules containing isopropyl myristate from whole milk and PGA Preparation of the aqueous phase: 400 mg of PGA are dissolved in 40 ml of whole milk.

Preparation of the hydrophobic phase: 3 ml of the alcoholic sodium hydroxide solution prepared as described in Example 1 are added to 3 ml of isopropyl myristate and the two are mixed by magnetic agitation for 2 min.

Emulsification: 6 ml of the hydrophobic phase are emulsified as the disperse phase in 40 ml of the aqueous phase by agitation at 2000 rpm.

After 15 min, neutralization is effected by the addition of 3 ml of the acid alcoholic solution prepared as described in Example 1.

After 15 min, the reaction medium is diluted by the addition of 40 ml of distilled water and agitation for 1 min. The microcapsules are then washed several times with distilled water.

This gives spherical microcapsules of mean size 5 µm.

EXAMPLE 29

According to the Invention

Manufacture of microcapsules containing isopropyl myristate from ovalbumin and PGA Preparation of the aqueous phase: 4 g of ovalbumin and 400 mg of PGA are dissolved in 40 ml of distilled water.

Preparation of the hydrophobic phase: 4 ml of the alcoholic sodium hydroxide solution prepared as described in Example 1 are added to 8 ml of isopropyl myristate and the two are mixed by magnetic agitation for 2 min.

Emulsification: 12 ml of the hydrophobic phase are emulsified as the disperse phase in 40 ml of the aqueous phase by agitation at 2000 rpm.

After 15 min, neutralization is effected by the addition of 4 ml of an acid solution prepared as described in Example 1. After 15 min, washes are effected as described in Example 15.

This gives spherical microcapsules of mean size 15 µm. If the microcapsules are crushed by the application of pressure to the microscope cover slip, the oily droplet is seen under the microscope to come out of the membrane.

EXAMPLE 30

According to the Invention

Manufacture of microcapsules from egg yolk and PGA

The aqueous phase is prepared by dissolving 80 mg of PAG in 8 ml of egg yolk by agitation.

The protocol described in Example 1 is then repeated using 6 ml of the above solution as the aqueous phase.

This gives beige-colored microcapsules of mean size 300 µm after freezing and lyophilization. After lyophilization, rehydration of the powder obtained from microcapsules shows that the microcapsules are intact and resume their spherical shape.

EXAMPLE 31

According to the Invention

Manufacture of microcapsules with an aqueous internal phase from a protein grafted with a long hydrocarbon chain, for example Lamepon S®, in solution in a hydrophobic liquid and PGA in aqueous solution The aqueous phase is prepared by dissolving 160 mg of PGA in 8 ml of distilled water.

The hydrophobic phase is prepared by dissolving 3 g of a protein grafted with a long hydrocarbon chain, or a commercially available polyamide, for example the one known under the tradename Lamepon S® (a product well known to those skilled in the art, available from LASERSON et SABETAY), in 30 ml of chloroform.

Emulsification is carried out by emulsifying 6 ml of the aqueous phase as the disperse phase in 30 ml of the hydrophobic phase by agitation at 2000 rpm for 5 min.

Alkalization, acidification and washing are then effected as described in Example 1.

This gives spherical microcapsules of mean size 30 µm.

EXAMPLE 32

According to the Invention

Manufacture of microcapsules from chitosan and PGA

The aqueous phase is prepared by dissolving 400 mg of chitosan, for example the product commercially available under the tradename Seacur 143 from PROTAN, in 10 ml of 1M acetic acid, then adjusting the pH to 5.6 with sodium hydroxide and then dissolving 100 mg of PGA in this solution.

The protocol described in Example 1 is then repeated using the above solution as the aqueous phase.

This gives a bulky sediment formed of microcapsules with a well-defined membrane and a diameter of between 50 and 500 µm.

What is claimed is:

1. Microparticles comprising an outer wall comprising the reaction product of a polysaccharide carrying esterified carboxyl groups and an organic substance which performs a transacylation reaction with said polysaccharide, selected from the group consisting of a polyamine substance and a polyhydroxylic substance.

2. Microparticles according to claim 1, wherein the ratio between said esterified polysaccharide and said polyamine substance ranges between 0.04 and 60% per weight.

3. Microparticles according to claim 1, wherein the ratio between said esterified polysaccharide and said polyhydroxylic substance ranges between 5 and 300% per weight.

4. Microparticles according to claim 1, wherein said esterified polysaccharide comprises at least 50% of its carboxyl groups esterified.

5. Microparticles according to claim 1, wherein said esterified polysaccharide is selected from the group consisting of propylene glycol alginate and pectins.

6. Microparticles according to claim 1, wherein said polyamine is selected form the group consisting of a polysaccharide carrying amine groups, chitosan, and a protein.

7. Microparticles according to claim 1, having a diameter ranging between about 0.1 µm and about 5000 µm.

8. Microparticles according to claim 1, wherein said microparticles contain an active principle selected from the group consisting of a cosmetic active principle, a pharmaceutical active principle, a foodstuff active principle, a substance possessing a biological activity, a protein, an enzyme and hemoglobin.

9. Microparticles according to claim 1, wherein said microcapsules comprise microcapsules.

10. Microparticles according to claim 9, wherein said microcapsules comprise said outer wall surrounding an inner space comprising an encapsulated aqueous phase.

11. Microparticles according to claim 9, wherein said microparticles comprise microcapsules having said outer wall surrounding an inner space comprising an encapsulated oily phase.

12. A process for the manufacture of microparticles, which comprises the following successive steps:

a) preparing a substantially neutral aqueous solution containing a polysaccharide carrying esterified carboxyl groups, and a substance which performs a transacylation reaction with said polysaccharide, selected from the group consisting of a polyamine and a polyhydroxylic substance;

b) providing a hydrophobic liquid in which the esterified polysaccharide and the polyamine are essentially insoluble;

c) mixing the hydrophobic liquid and the aqueous solution to form an emulsion;

d) adding a solution of an alkaline substance in an organic liquid miscible with the aqueous phase to the hydrophobic liquid provided under b) or to the emulsion formed under c); and e) maintaining the contacting of said solution of alkaline substance in said organic liquid with said hydrophobic liquid for a period of time sufficient to form said microparticles.

13. The process of claim 12, wherein after said period of time for forming said microparticles, said emulsion is neutralized by the addition to the emulsion of a solution of an acid substance in an organic medium miscible with the aqueous phase thereby neutralizing and stabilizing the microparticles formed and then separating said microparticles from said reaction medium.

14. The process of claim 13, wherein when the aqueous solution forms a dispersed phase in the hydrophobic liquid as the continuous phase, the solution of alkaline substance in the organic liquid miscible with the aqueous phase is added to the emulsion.

15. The process of claim 12, wherein the hydrophobic phase forms a dispersed phase in the neutral aqueous solution as the continuous phase, the solution of alkaline substance in the organic liquid miscible with the aqueous phase is added to the hydrophobic liquid.

16. The process of claim 12, wherein said particles comprise microcapsules having a filled inner space.

17. The process of claim 16, wherein said filled inner space comprises a phase selected from the group consisting of an aqueous phase, an oily phase and bubbles of a gas.

18. A process according to claim 17, whereto said inner space comprises one or more active principles selected from the group consisting of a cosmetic active principle, a pharmaceutical active principle, a foodstuff active principle and an active principle having a biological activity.

19. A process for the manufacture of microparticles, which comprises the following successive steps:

(a) preparing a substantially neutral aqueous solution of a polysaccharide carrying esterified carboxyl groups;

(b) preparing a hydrophobic solution of a substance capable of reacting with said polysaccharide selected from the group consisting of a polyamine substance and a polyhydroxylic substance, in a hydrophobic liquid in which the esterified polysaccharide is essentially insoluble;

(c) preparing a solution of an alkaline agent in an organic liquid miscible with the aqueous phase;

(d) mixing the solution of the alkaline agent in the organic liquid miscible with the aqueous phase with said hydrophobic solution prepared under (b), thereby getting a hydrophobic phase;

(e) forming an emulsion of the hydrophobic phase as the dispersed phase in the neutral aqueous solution of the esterified polysaccharide as the continuous phase and allowing a transacylation reaction to develop on the surface of the dispersed droplets of said hydrophobic phase by diffusion of the alkaline ions to the interface during a period of time sufficient to form said microparticles; and (f) adding to said emulsion a solution of an acid substance in a solvent selected from the group consisting of an organic liquid miscible with the aqueous phase and water thereby neutralizing and stabilizing said microparticles.

20. The process of claim 19, wherein said transacylation reaction is performed during a period of time sufficient to prepare microcapsules comprising a filled inner space.

21. A substantially process for the manufacture of microparticles comprising the following successive steps:
   (a) preparing a neutral aqueous solution of polysaccharide carrying esterified carboxyl groups;
   (b) preparing a solution of a core acting substance capable of reacting with said polysaccharide, selected from the group consisting of a polyamine substance and a polyhydroxylic substance, in a hydrophobic liquid in which the esterified polysaccharide is essentially insoluble;
   (c) forming an emulsion of the aqueous solution as the disperse phase in the hydrophobic liquid as the continuous phase;
   (d) adding to the emulsion a solution of an alkaline substance in an organic liquid miscible with the aqueous phase to initiate an interfacial transacylation reaction which is performed during a period to time sufficient to form said microparticles; and
   (e) adding to the emulsion a solution of an acid substance in an organic liquid miscible with the aqueous phase to neutralize and stabilize the microparticles.

22. The process of claim 12, further comprising recovering the microparticles and placing said microparticles in an aqueous or alcoholic solution of lime to initiate the reaction between the functional groups of the esterified polysaccharide and calcium ions.

23. The process of claim 19, further comprising recovering the microparticles and placing said microparticles in an aqueous or alcoholic solution of lime to initiate the reaction between the functional groups of the esterified polysaccharide and calcium ions.

24. The process of claim 21, further comprising recovering the microparticles and placing said microparticles in an aqueous or alcoholic solution of lime to initiate the reaction between the functional groups of the esterified polysaccharide and calcium ions.

25. The process of claim 12, wherein said polyamine substance is selected from the group consisting of a polysaccharide carrying amine groups, a protein, a protein partially hydrolyzed, a protein grafted with $C_{10}$–$C_{30}$ hydrocarbon chains, a protein containing free amine groups, milk, mixtures of atelocollagen and glycosaminoglycans, an albumin, ovalbumin, alpha-lactalbumin, globulins, fibrinogen, casein, glutelins, solubilized scleroproteins, collagen, atelocollagen, gelatin, hemoglobin, enzymes, whole milk, whey proteins, whole egg, egg yolk, a diamine, an alkylenediamine, a $C_2$–$C_6$ alkylenediamine, a diamine comprising an aromatic ring, an acyclic amine containing a ring nitrogen atom and an alkylenepolyamine.

26. The process of claim 25, wherein said alkylenediamine is selected from the group consisting of ethylenediamine, trimethylenediamine, tetramethylenediamine, pentamethylenediamine and hexamethylenediamine, said diamine comprising an aromatic ring is selected from the group consisting of m-phenylenediamine and p-phenylenediamine; said acyclic amine containing a ring nitrogen atom is piperazine; and said alkylenepolyamine is tetraethylenepentamine.

27. The process of claim 12, wherein said esterified polysaccharide is a hydrophilic polysaccharide carrying carboxyl groups, at least 50% of which are esterified.

28. A process according to claim 12, wherein said esterified polysaccharide is selected from the group consisting of propylene glycol alginate and pectins.

29. A process according to claim 12 wherein said polyhydroxylic substance is selected from the group consisting of a polysaccharide, a cellulose, a polyalcohol and an alkylene glycol.

30. The process of claim 29, wherein said polysaccharide is selected from the group consisting of starch, partially hydrolyzed starch, hydroxyethyl starch, carboxymethyl starch, sodium alginate, guar gum, gum arabic and gum tragacanth; said cellulose is selected from the group consisting of hydroxypropyl cellulose, carboxymethyl cellulose, ethyl cellulose, hydroxypropyl methyl cellulose and hydroxyethyl cellulose; said polyalcohol is a polyvinyl alcohol and said alkylene glycol is a $C_2$–$C_6$-alkylene glycol; said glycol group consisting of ethylene glycol, butane-1,4-diol, hexamethylene glycol and glycerol.

31. The process of claim 12, wherein said hydrophobic liquid is selected from the group consisting of isopropyl myristate, paraffin oil, cyclohexane, chloroform, dichloromethane, a natural glycerol, a synthetic glycerol, a vegetable oil, a fatty acid ester of an alcohol and mixtures thereof.

32. The process of claim 31, wherein said vegetable oil is selected from the group consisting of a groundnut oil, an olive oil and a colza oil, said fatty acid ester of an alcohol is selected from the group consisting of methyl oleate and ethyl oleate, and mixtures thereof.

33. The process of claim 12, wherein said alkaline organic liquid miscible with the aqueous phase is a solution of an hydroxide selected from the group consisting of sodium hydroxide and potassium hydroxide, in a solvent selected from the group consisting of pure alcohol, alcohol containing from 5 to 10% of water, and a polyol.

34. The process of claim 33, wherein said hydroxide solution comprises from 0.05 to 2% w/v of sodium hydroxide in 95% ethanol.

35. The process of claim 13, wherein said acid organic medium miscible with the aqueous phase is a solution of a carboxylic acid selected from the group consisting of a monocarboxylic organic acid, a polycarboxylic organic acid, and a mineral acid, in a solvent selected from the group consisting of pure alcohol, alcohol containing from 5 to 10% of water, and a polyol.

36. The process of claim 35, wherein said organic acid is selected from the group consisting of acetic acid, citric acid, lactic acid, tartaric acid, succinic acid and malic acid, and said mineral acid is hydrochloric acid; said alcohol is selected from the group consisting of methanol and ethanol; and said polyol is selected from the group consisting of glycerol and a polyethylene glycol.

37. The process of claim 36, wherein said acid solution is essentially consisting of 95% ethanol containing between 1 and 10% v/v of acetic acid.

38. The process of claim 12, wherein said emulsion is produced in presence of a surfactant.

39. The process of claim 38, wherein said surfactant is selected from the group consisting of a sorbitan ester, a lecithin and a polysorbate.

40. A composition selected from the group consisting of a cosmetic composition, a pharmaceutical composition, a food composition and an enzyme composition, comprising microparticles having an outer wall which is the reaction product of a substance consisting of a polyamine and a polyhydroxylic substance with a polysaccharide carrying esterified carboxyl groups.

41. The composition of claim 40, wherein said microparticles have a filled inner space comprising a phase selected from the group consisting of an aqueous phase, and hydrophobic phase and a phase comprising bubbles of a gas.

42. The composition of claim 41, wherein said phase contains one or several active principles selected from the group consisting of a cosmetic active principle, a pharmaceutical active principle, a foodstuff active principle and an enzyme.

43. Microparticles according to claim 1, wherein said esterified polysaccharide is propylene glycol alginate and said polyamine substance is human serum albumin.

44. Microparticles according to claim 1, wherein said esterified polysaccharide is propylene glycol alginate and said polyamine substance is ovalbumin.

45. Microparticles of claim 1, wherein said esterified polysaccharide is propylene glycol alginate and said polyamine substance is hemoglobin.

46. Microparticles according to claim 1, wherein said esterified polysaccharide is propylene glycol alginate and said polyamine substance is fibrinogen.

47. Microparticles according to claim 1, wherein said esterified polysaccharide is propylene glycol alginate and said polyamine substance is catalase.

48. Microparticles according to claim 1, wherein said esterified polysaccharide is propylene glycol alginate and said polyamine substance is gelatin.

49. Microparticles according to claim 1, wherein said esterified polysaccharide is propylene glycol alginate and said polyamine substance is an admixture of atelocollagen with chondroitin sulfate.

50. Microparticles according to claim 49, wherein said microparticles have further been subjected to a treatment with CaCl2.

51. Microparticles according to claim 1, wherein said microparticles comprise microcapsules, wherein said outer wall comprising the reaction product of atelocollagen, chondroitin sulfate and propylene glycol alginate, said outer wall surrounding an inner space filled with air bubbles.

52. Microparticles according to claim 1, wherein said esterified polysaccharide is propylene glycol alginate and said polyamine substance is selected from the group consisting of whole milk, skim milk, and whey protein.

53. Microparticles according to claim 1, wherein said esterified polysaccharide is propylene glycol alginate and said polyamine substance is hexamethylene diamine.

54. Microparticles according to claim 1, wherein said esterified polysaccharide is pectic with an esterification rate from 70 to 75% and said polyamine substance is ovalbumin.

55. Microparticles according to claim 1, wherein said esterified polysaccharide is pectic with an esterification rate of 70 to 75% and said polyamine substance is milk power.

56. Microparticles according to claim 1, wherein said esterified polysaccharide is propylene glycol alginate and said polyhydroxylic substance is selected from the group consisting of polyvinyl alcohol, hydroxyethyl starch, carboxymethyl cellulose, and hydroxy propyl cellulose.

57. Microparticles according to claim 1, comprising microcapsules containing an oily internal face, said esterified polysaccharide being propylene glycol alginate and said polyamine substance being hexamethylene diamine.

58. Microparticles according to claim 1, comprising microcapsules containing isopropylmiristad, said esterified polysaccharide is propylene glycol alginate and said polyamine substance is selected from the group consisting of whole milk and ovalbumin.

59. Microparticles according to claim 1, wherein said esterified polysaccharide is propylene glycol alginate and said polyamine substance is egg yolk.

60. Microparticles according to claim 1, comprising microcapsules with an aqueous internal phase, said esterflied polysaccharide is propylene glycol alginate and said polyamine substance is a protein graffing with a long hydrocarbon chain.

61. Microparticles according to claim 1, wherein said esterified polysaccharide is propylene glycol alginate and said polyhydroxylic substance is chitosan.

* * * * *

UNITED STATES PATENT AND TRADEMARK OFFICE
CERTIFICATE OF CORRECTION

PATENT NO. : 5,691,060
DATED : November 25, 1997
INVENTOR(S) : LEVY

It is certified that error appears in the above-indentified patent and that said Letters Patent is hereby corrected as shown below:

Column 13, line 3, after "mean diameter 75", please insert --$\mu$m--.

Example 31, column 20, lines 57-58, please delete "polyamide" and insert --polyamine--.

Claim 40, column 24, line 5, please delete "and" and insert --or--.

Claim 21, column 23, line 1, delete "substantially";
    line 3, after "preparing a" insert --substantially--.

Claim 54, column 26, line 2, delete "pectic" and insert --pectine--.

Claim 55, column 26, line 2, delete "pectic" and insert --pectine--;
    line 3, delete "milk power" and insert --milk powder--.

Claim 58, column 26, line 2, delete "isopropylmiristad" and insert --isopropylmiristat--.

UNITED STATES PATENT AND TRADEMARK OFFICE
CERTIFICATE OF CORRECTION

PATENT NO. : 5,691,060
DATED : November 25, 1997
INVENTOR(S) : LEVY

It is certified that error appears in the above-identified patent and that said Letters Patent is hereby corrected as shown below:

Claim 60, column 26, line 2, delete "esterflied" and insert --esterified--;
　　　　line 4, delete "graffing" and insert --grafted--.

Signed and Sealed this

Twenty-fourth Day of November, 1998

Attest:

BRUCE LEHMAN

Attesting Officer　　　Commissioner of Patents and Trademarks